(12) United States Patent
Hoeink

(10) Patent No.: US 10,329,904 B2
(45) Date of Patent: Jun. 25, 2019

(54) DETERMINING THE ROBUSTNESS OF DISCRETE FRACTURE NETWORK PERMEABILITY ESTIMATES

(71) Applicant: Tobias Hoeink, Houston, TX (US)

(72) Inventor: Tobias Hoeink, Houston, TX (US)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 334 days.

(21) Appl. No.: 15/074,621

(22) Filed: Mar. 18, 2016

(65) Prior Publication Data

US 2017/0268332 A1 Sep. 21, 2017

(51) Int. Cl.

| | |
|---|---|
| *E21B 49/00* | (2006.01) |
| *E21B 49/02* | (2006.01) |
| *E21B 43/26* | (2006.01) |
| *E21B 7/04* | (2006.01) |
| *E21B 41/00* | (2006.01) |
| *E21B 43/00* | (2006.01) |
| *G01N 15/08* | (2006.01) |
| *E21B 33/13* | (2006.01) |
| *E21B 37/00* | (2006.01) |
| *E21B 43/20* | (2006.01) |
| *E21B 43/24* | (2006.01) |
| *E21B 43/25* | (2006.01) |

(52) U.S. Cl.
CPC ............... *E21B 49/00* (2013.01); *E21B 7/04* (2013.01); *E21B 41/0092* (2013.01); *E21B 43/00* (2013.01); *E21B 49/02* (2013.01); *G01N 15/08* (2013.01); *E21B 33/13* (2013.01); *E21B 37/00* (2013.01); *E21B 43/20* (2013.01); *E21B 43/24* (2013.01); *E21B 43/25* (2013.01); *E21B 43/26* (2013.01); *G01N 15/0806* (2013.01)

(58) Field of Classification Search
None
See application file for complete search history.

(56) References Cited

U.S. PATENT DOCUMENTS

| | | | |
|---|---|---|---|
| 6,023,656 | A | 2/2000 | Cacas et al. |
| 2005/0015231 | A1 | 1/2005 | Edwards et al. |
| 2008/0133186 | A1 | 6/2008 | Li et al. |

(Continued)

FOREIGN PATENT DOCUMENTS

WO    2012015517 A1    2/2012

OTHER PUBLICATIONS

Ahmed Eifeel, M; Static and Dynamic Assessment of DFN Permeability Upscaling (EAGE Annual Conference & Exhibition, Jun. 2012.*

(Continued)

*Primary Examiner* — Charles D Garber
*Assistant Examiner* — Alia Sabur
(74) *Attorney, Agent, or Firm* — Cantor Colburn LLP

(57) ABSTRACT

Examples of techniques for determining robustness of a discrete fracture network (DFN) permeability estimate are disclosed. In one example implementation according to aspects of the present disclosure, a method may include: receiving a DFN of an earth formation of interest, the DFN comprising a plurality of connected fractures; determining a directional equivalent permeability of the plurality of connected fractures of the DFN using a numerical upscaling method; and determining the robustness of the directional equivalent permeability.

14 Claims, 6 Drawing Sheets

(56) References Cited

U.S. PATENT DOCUMENTS

| | | | |
|---|---|---|---|
| 2009/0125239 A1 | 5/2009 | Niemeyer et al. | |
| 2010/0155142 A1 | 6/2010 | Michael et al. | |
| 2010/0185427 A1 | 7/2010 | Tilke et al. | |
| 2012/0116740 A1* | 5/2012 | Fourno | E21B 43/00 703/10 |
| 2013/0054207 A1 | 2/2013 | Souche et al. | |
| 2013/0096900 A1 | 4/2013 | Usadi et al. | |
| 2013/0340997 A1 | 12/2013 | Zupanick | |
| 2014/0076543 A1 | 3/2014 | Ejofodomi et al. | |
| 2014/0372095 A1 | 12/2014 | Van der Zee et al. | |
| 2016/0215594 A1* | 7/2016 | Hoeink | E21B 41/0092 |
| 2017/0096880 A1 | 4/2017 | Ben et al. | |
| 2017/0175507 A1* | 6/2017 | Hoeink | E21B 43/26 |

OTHER PUBLICATIONS

Teimoori, Ahmed & Chen, Zhixi & S. Rahman, Sheik & Tran, T. (2005). Effective Permeability Calculation Using Boundary Element Method in Naturally Fractured Reservoirs. Petroleum Science and Technology. 23. 693-709. 10.1081/LFT-200033029.*

Factoring Anisotropy into Well Design, Oilfield Review, vol. 2, Issue 4 (1990).*

Al-Hadrami, Hamoud & Teufel, L.W. (2000). Influence of Permeability Anisotropy and Reservoir Heterogeneity on Optimization of Infill Drilling in Naturally Fractured Tight-Gas Mesaverde Sandstone Reservoirs, San Juan Basin. 10.2523/60295-MS.*

He, Ji & Chen, Sheng-hong & Shahrour, Isam. (2013). Numerical estimation and prediction of stress-dependent permeability tensor for fractured rock masses. International Journal of Rock Mechanics and Mining Sciences. 59. 70-79. 10.1016/j.ijrmms.2012.12.001.*

International Search Report and the Written Opinion of the International Searching Authority; PCT/US2017/022894; Korean Intellectual Property Office; dated Jun. 8, 2017; 9 pages.

International Search Report and the Written Opinion of the International Searching Authority, or the Declaration; PCT/US2016/054131; dated Jan. 2, 2017; 12 pages.

Oda, M.,"Permeability Tensor for Discontinuous Rock Masses.", Geotechnique, vol. 35, No. 4, pp. 483-495, Dec. 1985.

Salimi, et al.; Upscaling of Fractured Oil Reservoirs Using Homogenization Including Non-Equilibrium Capillary Pressure and Relative Permeability; 2012; Retrieved from the internet; URL: https://www.researchgate.net/publication/254903947_Upscaling_of_Fractured_Oil_Reservoirs_Using_Homogenization_Including_Non-equilibrium_Capillary_Pressure; 23 pages.

* cited by examiner

DETERMINING THE ROBUSTNESS OF DISCRETE FRACTURE NETWORK PERMEABILITY ESTIMATES

BACKGROUND

The present disclosure relates to discrete fracture networks and, more particularly, to determining the robustness of discrete fracture network permeability estimates.

Boreholes are drilled into earth formations having reservoirs of hydrocarbons in order to extract the hydrocarbons through the boreholes to the surface. Selecting a location at which to drill a borehole is largely dependent on the permeability of the earth formation or ability to flow fluids through pores and fractures of the earth formation. Numerical computational approaches have been used to simulate fractured reservoirs. Typically, these methods are computational time intensive and may cause certain variables to be ignored for simplicity.

Upscaling techniques are often utilized in order to obtain the equivalent permeability of a DFN. Upscaling techniques include an analytical method proposed by M. Oda (see Oda, M., 1985, "Permeability Tensor for Discontinuous Rock Masses.", Geotechnique, Vol. 35, pp. 483-495) and a range of numerical methods with different applied boundary conditions. Oda's method is an analytical method and hence it is fast. However, it neglects the connectivity between fractures and is not valid for less connected DFNs. Numerical methods for calculating permeability on the other hand depend on the boundary conditions across the DFN, and require more computation time than Oda's method.

BRIEF SUMMARY

According to examples of the present disclosure, techniques including methods, systems, and/or computer program products for determining robustness of a discrete fracture network (DFN) permeability estimate are provided. An example method may include: receiving a DFN of an earth formation of interest, the DFN comprising a plurality of connected fractures; determining a directional equivalent permeability of the plurality of connected fractures of the DFN using a numerical upscaling method; and determining the robustness of the directional equivalent permeability.

According to additional examples of the present disclosure, an example system may include: a memory having computer readable instructions; and a processing device for executing the computer readable instructions. The computer readable instructions may include: receiving a DFN of an earth formation of interest, the DFN comprising a plurality of connected fractures; determining a first directional equivalent permeability of the plurality of connected fractures of the DFN using a numerical upscaling method; determining a second directional equivalent permeability of the plurality of connected fractures of the DFN using Oda's method; determining a robustness of the first directional equivalent permeability by comparing the first directional equivalent permeability to the second directional equivalent permeability; and performing an action relating to the earth formation of interest using the first directional equivalent permeability.

Additional features and advantages are realized through the techniques of the present disclosure. Other aspects are described in detail herein and are considered a part of the disclosure. For a better understanding of the present disclosure with the advantages and the features, refer to the following description and to the drawings.

BRIEF DESCRIPTION OF THE DRAWINGS

The subject matter which is regarded as the invention is particularly pointed out and distinctly claimed in the claims at the conclusion of the specification. The foregoing and other features, and advantages thereof, are apparent from the following detailed description taken in conjunction with the accompanying drawings in which:

DETAILED DESCRIPTION

Various implementations are described below by referring to several examples of determining the robustness of discrete fracture network (DFN) permeability estimates. A DFN represents a series of fractures of an earth formation of interest. A DFN is a set of fractures that forms a representation of a large set of possible representations, which comply with a set of characteristics, such as average and standard deviations of fracture orientation, length, height, and aperture (width). A DFN may hold connectivity information (i.e., information such as which fracture is connected to which other fracture). A DFN does not necessarily correlate one-to-one to an existing fracture network in the subsurface. That is, the DFN may not describe existing fractures, but may instead describe fracture characteristics in some average or macro sense. A DFN is useful in evaluating whether to perform well operations at the earth formation of interest. For example, a DFN that indicates a series of connected fractures may indicate a desirable location for performing well operations, while a DFN that does not indicate that the series of fractures are connected (or are less connected than another DFN) may be less desirable for performing well operations. DFNs are derived from core sample of an earth formation of interest. For example, a core sample is extracted from the earth formation of interest and analyzed to identify fractures within the core sample. The DFN represents the identified fractures from the core sample.

The present techniques utilize fewer computational resources than prior approaches to assess the robustness of a directional equivalent permeability of connected fractures of a DFN, such as those involving a large number of Monte-Carlo operations. Accordingly, the present techniques enable a processing system to operate more efficiently and to determine robustness more quickly than prior approaches. The present techniques account for more parametric aspects of DFN robustness determination than prior approaches. These and other advantages will be apparent from the description that follows.

The teachings of the present disclosure can be applied in a variety of well operations. These operations may involve using one or more treatment agents to treat a formation, the fluids resident in a formation, a wellbore, and/or equipment in the wellbore, such as production tubing. The treatment agents may be in the form of liquids, gases, solids, semi-solids, and mixtures thereof. Illustrative treatment agents include, but are not limited to, fracturing fluids, acids, steam, water, brine, anti-corrosion agents, cement, permeability modifiers, drilling muds, emulsifiers, demulsifiers, tracers, flow improvers etc. Illustrative well operations include, but are not limited to, hydraulic fracturing, stimulation, tracer injection, cleaning, acidizing, steam injection, water flooding, cementing, etc.

Figure 1:
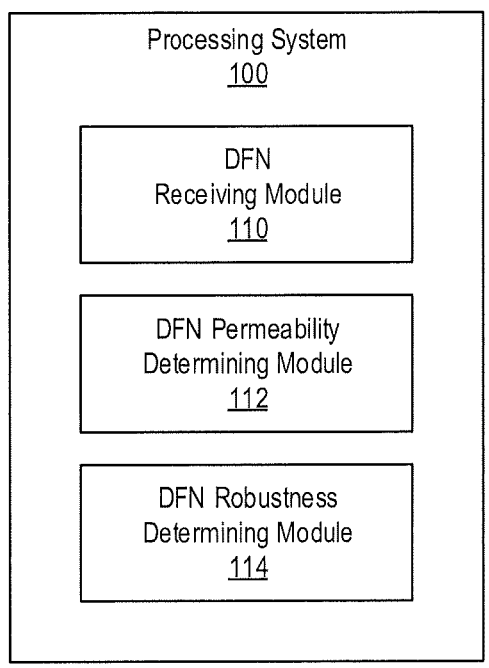
FIG. 1 illustrates a block diagram of a processing system for determining the robustness of a discrete fracture network permeability estimate according to aspects of the present disclosure.

FIG. 1 illustrates a block diagram of a processing system 100 according to examples of the present disclosure. The various components, modules, engines, etc. described regarding FIG. 1 may be implemented as instructions stored on a computer-readable storage medium, as hardware modules, as special-purpose hardware (e.g., application specific hardware, application specific integrated circuits (ASICs), as embedded controllers, hardwired circuitry, etc.), or as some combination or combinations of these. In examples, the engine(s) described herein may be a combination of hardware and programming. The programming may be processor executable instructions stored on a tangible memory, and the hardware may include processing device 101 for executing those instructions. Thus a system memory can store program instructions that when executed by a processing device implement the modules described herein. Other modules may also be utilized to include other features and functionality described in other examples herein.

In aspects of the present disclosure, processing system 100 includes a DFN receiving module 110, a DFN permeability determining module 112, and a DFN robustness determining module 114. Alternatively or additionally, the processing system 100 may include dedicated hardware, such as one or more integrated circuits, Application Specific Integrated Circuits (ASICs), Application Specific Special Processors (ASSPs), Field Programmable Gate Arrays (FPGAs), or any combination of the foregoing examples of dedicated hardware, for performing the techniques described herein.

The DFN receiving module 110 receives a DFN that is representative of an earth formation of interest. In particular, the DFN represents fractures identified during an analysis of a core sample of the earth formation of interest. For example, FIG. 2A illustrates a top view of an example DFN 202, and FIG. 3A illustrates a top view of an alternate example DFN 302.

The DFN permeability determining module 112 determines a directional equivalent permeability of the fractures of the DFN. In examples, the DFN permeability determining module 112 determines multiple directional equivalent permeabilities using different methods. For example, the DFN permeability determining module 112 determines a first directional equivalent permeability using a numerical upscaling method. For example, a perfect fit analysis can be used in which the DFN is cropped to the volume of interest after rotation. In another example, the DFN is cropped to the volume of interest before rotation, and a second directional equivalent permeability is determined using Oda's method. The directional equivalent permeability provides guidance when evaluating a potential earth formation, including determining how much reservoir volume is accessible by connected fractures, determining how many connected fractures are connected to a wellbore, determining a principal direction of permeability of connected fractures, and determining an upscale DFN permeability value across the reservoir.

Figure 2A:
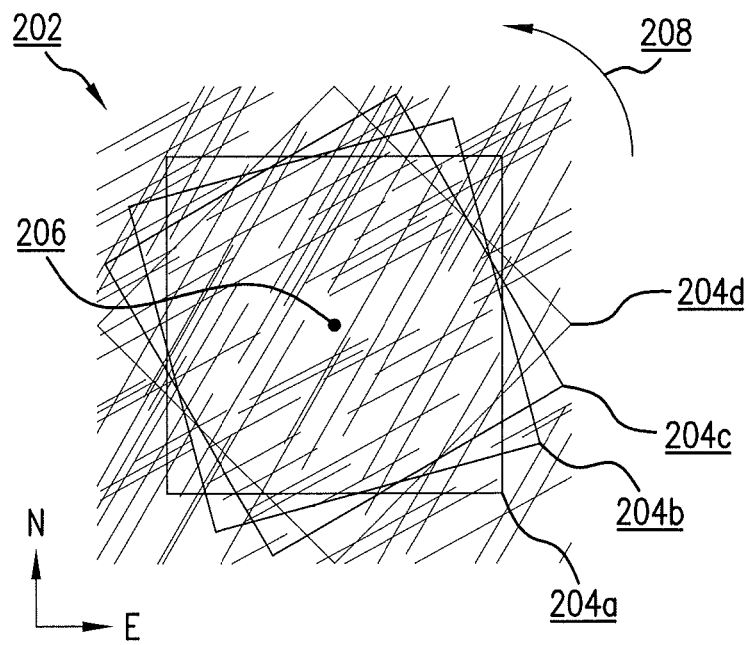
FIG. 2A illustrates a top view of an example DFN according to aspects of the present disclosure.
Figure 3A:
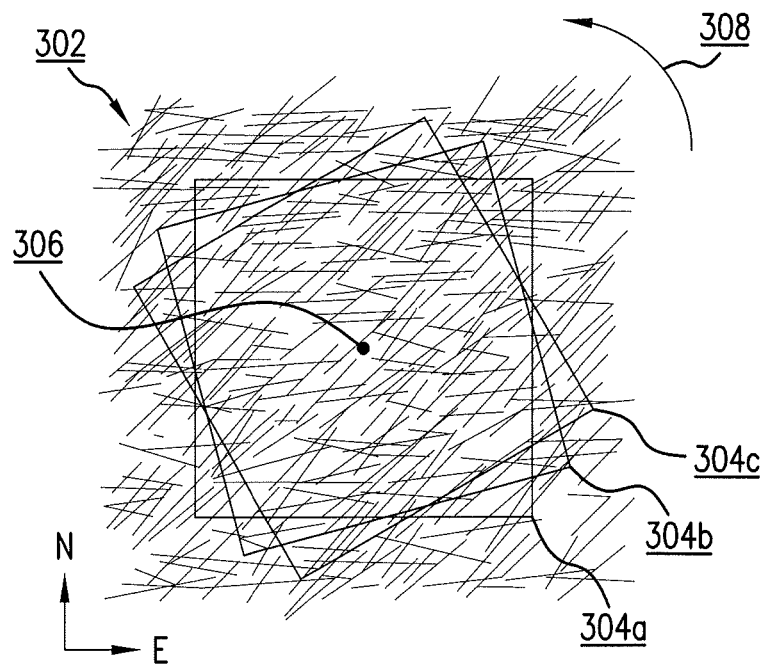
FIG. 3A illustrates a top view of an alternate example DFN according to aspects of the present disclosure.

As illustrated in FIG. 2A, the DFN permeability determining module 112 of FIG. 1 performs a numerical upscaling method (e.g., a perfect fit analysis) on the DFN 202. The DFN permeability determining module 112 captures a series of slices 204a, 204b, 204c, 204d taken incrementally about a center point 206. In the example of FIG. 2A, the DFN permeability determining module 112 captures slices at 15 degree increments about the center point 206 continuing 360 degrees about the center point 206 in a counter-clockwise direction as indicated by arrow 208. However, it should be appreciated that different increments may be utilized (e.g., 1 degree, 5 degrees, 12 degrees, 30 degrees, etc.). Although sampling squares are used for capturing slices 204a, 204b, 204c, the DFN permeability determining module 112 may apply other shapes to capture slices in aspects of the present disclosure. Moreover, the slices 204a, 204b, 204c, 204d may be taken in a clockwise direction in examples. Similarly, as illustrated in FIG. 3A, the DFN permeability determining module 112 performs a numerical upscaling method (e.g., a perfect fit analysis) on the DFN 302 by capturing a series of slices 304a, 304b, 304c at 15 degree increments about a center point 306 in a counter-clockwise direction as indicated by arrow 308.

Figure 2B:
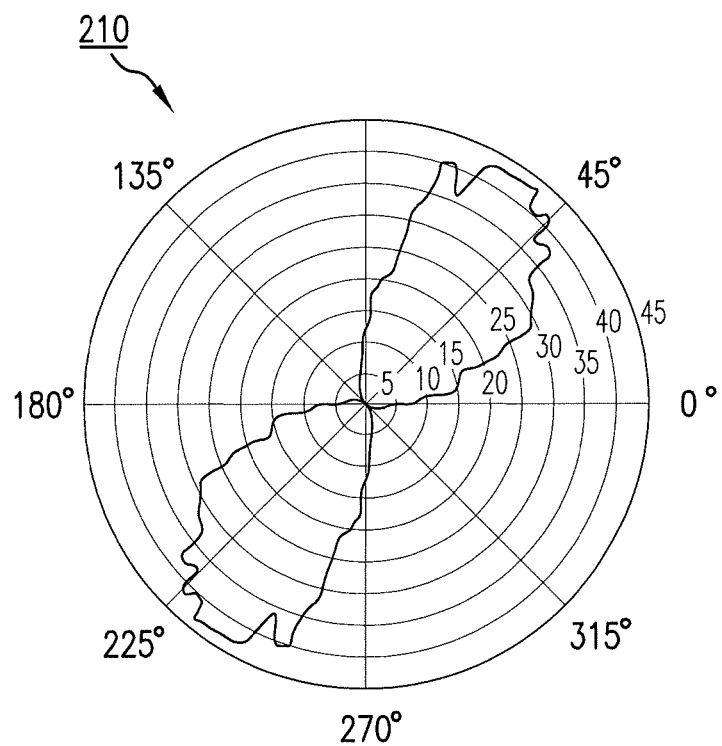
FIG. 2B illustrates a graph of a directional equivalent permeability for the example DFN of FIG. 2A according to aspects of the present disclosure.
Figure 3B:
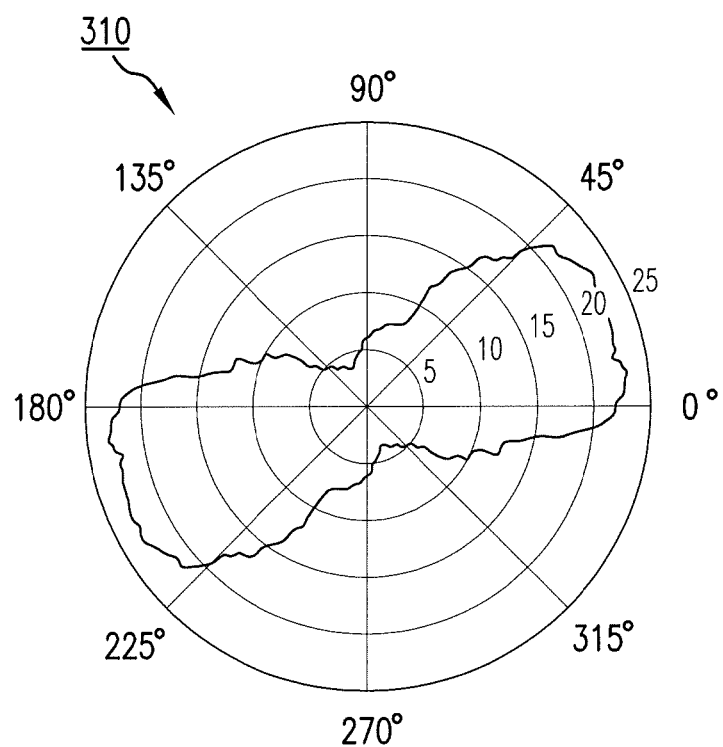
FIG. 3B illustrates a graph of a directional equivalent permeability for the alternate example DFN of FIG. 3A according to aspects of the present disclosure.

The DFN permeability determining module 112 then determines a directional equivalent permeability of the connected fractures of the DFNs 202, 302 using the slices 204a, 204b, 204c, 204d and 304a, 304b, 304c respectively. For example, FIG. 2B illustrates a directional equivalent probability 210 of the DFN 202 generated by the numerical upscaling method. The directional equivalent probability 210 is plotted on a polar graph, which plots the relative orientation of the fractures od the DFN 202 in degrees (zero degrees represents east, 90 degrees represents north, etc.) versus the permeability of the DFN 202 in units mDarcy. Similarly, FIG. 3B illustrates a directional equivalent probability 310 of DFN 302 resulting from the numerical upscaling method and plotted on a polar graph.

Once the directional equivalent permeabilities are determined, the DFN robustness determining module 114 determines a robustness of the first directional equivalent permeability by comparing the first directional equivalent permeability to a second directional equivalent permeability determined using Oda's method, which is discussed below.

In another embodiment, the graphical representation of the directional equivalent permeability can be used to quantify its robustness. In one example, the number of steps and the step size between neighboring angles can be used to compute a variance measure, which effectively quantifies the robustness. This enables the direct comparison, and further analysis, of any number of directional equivalent permeabilities, which can be obtained from different DFN's or from one DFN with different upscaling methods.

Figure 4:
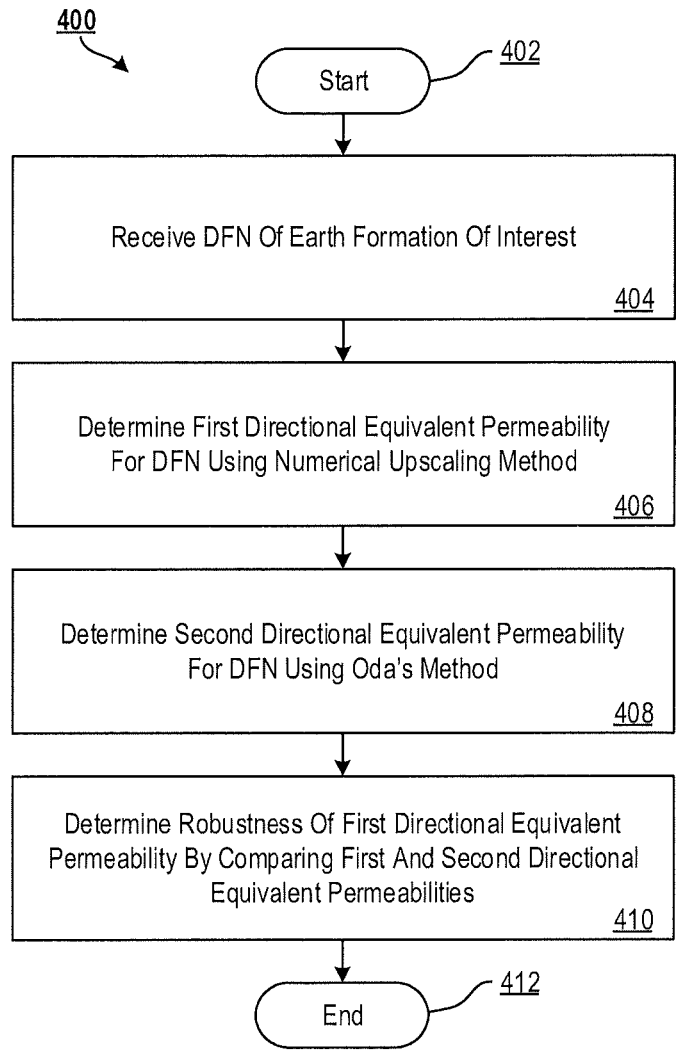
FIG. 4 illustrates a flow diagram of a method for determining the robustness of a discrete fracture network permeability estimate according to aspects of the present disclosure.

In particular, FIG. 4 illustrates a flow diagram of a method 400 for determining the robustness of a discrete fracture network permeability estimate according to examples of the present disclosure. The method 200 may be performed by a processing system, such as the processing system 100 of FIG. 1 and/or the processing system 20 of FIG. 6, or by another suitable processing system. In describing the method 400, the modules of the processing system 100 of FIG. 1 are referenced; however, such reference is not intended to be limiting. The method 400 starts at block 402 and continues to block 404.

Figures 5A, 5B, 5C:
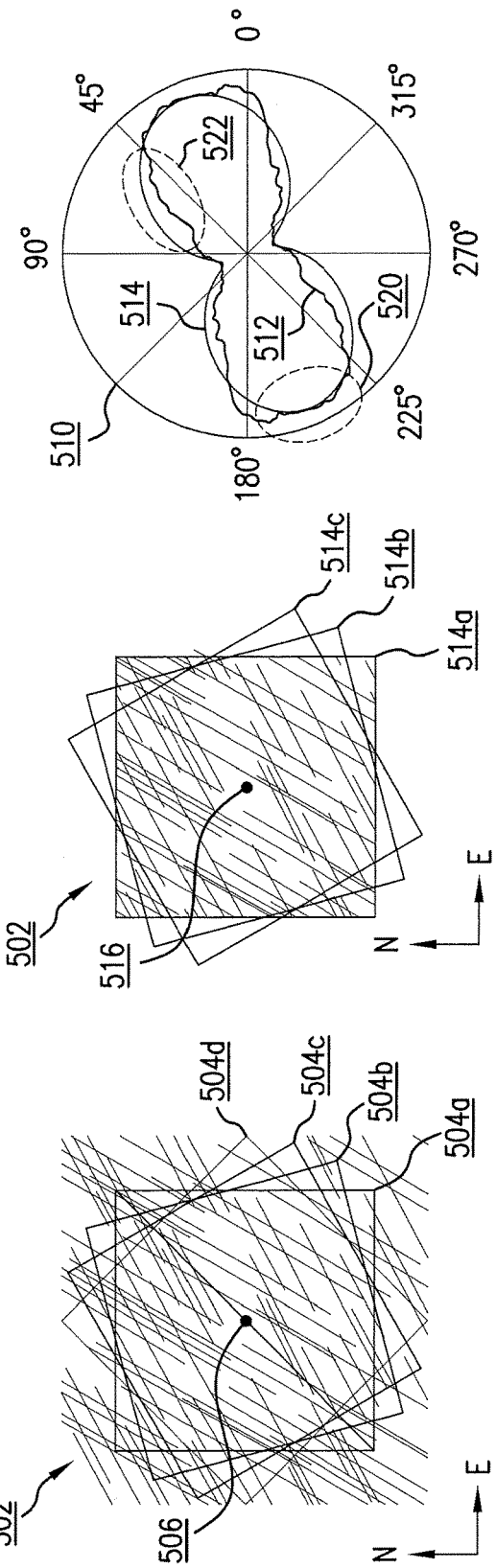
FIG. 5A illustrates a top view of another alternate example DFN having a numerical upscaling method applied thereto according to aspects of the present disclosure.
FIG. 5B illustrates a top view of the alternate example DFN of FIG. 5A having Oda's method applied thereto according to aspects of the present disclosure.
FIG. 5C illustrates a graph of a first directional equivalent permeability and a second directional equivalent permeability for the alternate example DFN of FIG. 5A according to aspects of the present disclosure.

At block 404 of the method 400, the DFN receiving module 110 receives a DFN that is representative of an earth formation of interest. FIG. 5A illustrates a top view of DFN 502 oriented with respect to known geographic directions (i.e., north, east). The DFN 502 comprises a group of line segments that intersect at various points and represent fractures of the earth formation of interest. It should be appreciated that the length, width, orientation, and connectivity of each of the segments (i.e., fractures) varies within the DFN 502.

At block 406 of the method 400, the DFN permeability determining module 112 performs a numerical upscaling method on the DFN 502 to determine a first directional equivalent permeability. The DFN permeability determining module 112 captures a series of slices 504a, 504b, 504c, 504d taken incrementally about a center point 506. In the example of FIG. 5A, the DFN permeability determining module 112 captures slices at 15 degree increments about the center point 506 continuing 360 degrees about the center point 506 in a counter-clockwise direction. The resulting first directional equivalent probability 512 is plotted on a polar graph 510, which plots the relative orientation in degrees (zero degrees represents east, 90 degrees represents north, etc.) versus the permeability of the DFN 202 in units mDarcy.

At block 408 of the method 400, the DFN permeability determining module 112 performs Oda's method on the DFN 502 to determine a second directional equivalent permeability. The DFN permeability determining module 112 captures a series of slices 514a, 514b, 514c, taken incrementally about a center point 516 of the DFN 502. In the example of FIG. 5B, the DFN permeability determining module 112 captures slices at 15 degree increments about the center point 516 continuing 360 degrees about the center point 516 in a counter-clockwise direction. When applying Oda's method, the DFN 502 is cropped to fit the slices. For example, as illustrated in FIG. 5A, the DFN 502 is cropped to fit slice 514a. The DFN permeability determining module 112 captures the additional slices (e.g., slices 514b, 514c, etc.) rotate about the center point 516 while utilizing this cropping. The resulting second directional equivalent probability 514 is plotted on the polar graph 510 along with the first directional equivalent probability 512. As illustrated in FIG. 5C.

At block 410 of the method 400, the DFN robustness determining module 114 determines a robustness of the first direction equivalent permeability 512 by comparing the first directional equivalent permeability 512 to the second directional equivalent permeability 514. As illustrated in FIG. 5C, the first directional equivalent permeability 512 and the second directional equivalent permeability 514 are plotted on the polar graph 510. In the present example, the DFN 502 has a principle direction of permeability along approximately 30 degrees, which represents an east-north-east direction.

Comparing the first directional equivalent permeability 512 to the second directional equivalent permeability 514 comprises calculating a difference between the first directional equivalent permeability 512 and the second directional equivalent permeability 514. The difference represents a difference in a smoothness of a graphical representation of the first directional equivalent permeability 512 and the second directional equivalent permeability 514. The difference in the smoothness between the first directional equivalent permeability 512 and second directional equivalent permeability 514 is a direct measure of the robustness of the connectivity of the fractures of the DFN 502 and of the robustness of the first equivalent permeability estimate 512. For example, region 520 of FIG. 5C illustrates a more robust first equivalent permeability estimate 512 while region 522 illustrates a less robust first equivalent permeability estimate 512.

The method 400 continues to block 412 and ends. However, additional processes also may be included. For example, the method 400 may include collecting a core sample of the earth formation of interest, and generating the DFN of the earth formation of interest from the core sample.

In addition, the method 400 may also include performing an action relating to the earth formation of interest using the first directional equivalent permeability. The action may include, for example, aligning a tool such as a drill in a direction determined by the first directional equivalent permeability. The action may also include performing in-fill drilling in a direction determined by the first directional equivalent permeability. The action may further include performing a reservoir stimulation in a direction determined by the first directional equivalent permeability.

In additional aspects of the present disclosure, the method 400 may be applied to a number of test cases to build a calibrated model of the smoothness-robustness relation to aid in the future assessment of DFN permeability robustness. It should be understood that the processes depicted in FIG. 5 represent illustrations, and that other processes may be added or existing processes may be removed, modified, or rearranged without departing from the scope and spirit of the present disclosure.

Figure 6:
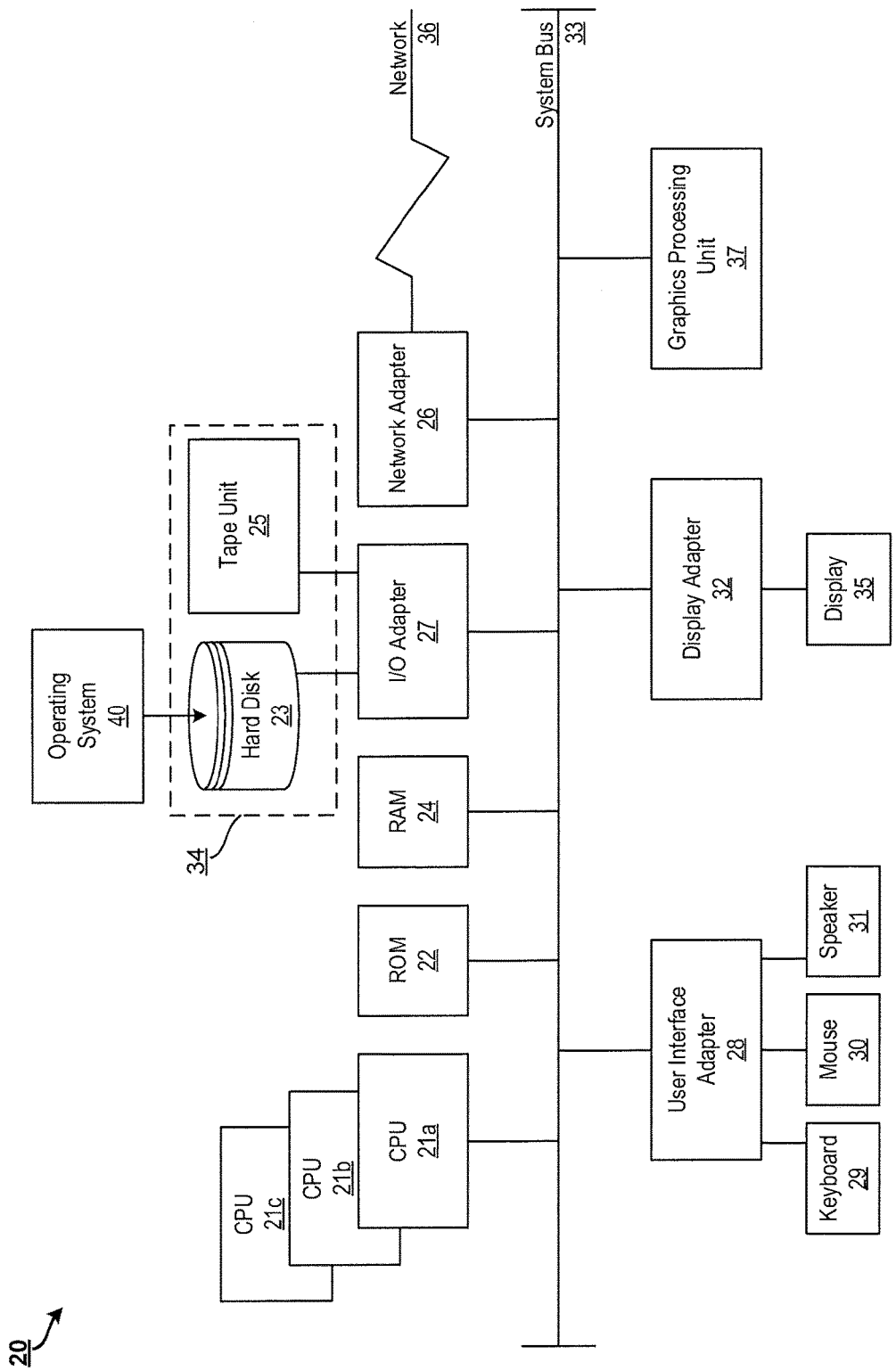
FIG. 6 illustrates a block diagram of a processing system for implementing the techniques described herein according to examples of the present disclosure.

It is understood in advance that the present disclosure is capable of being implemented in conjunction with any other type of computing environment now known or later developed. For example, FIG. 6 illustrates a block diagram of a processing system 20 for implementing the techniques described herein. In examples, processing system 20 has one or more central processing units (processors) 21a, 21b, 21c, etc. (collectively or generically referred to as processor(s) 21 and/or as processing device(s)). In aspects of the present disclosure, each processor 21 may include a reduced instruction set computer (RISC) microprocessor. Processors 21 are coupled to system memory (e.g., random access memory (RAM) 24) and various other components via a system bus 33. Read only memory (ROM) 22 is coupled to system bus 33 and may include a basic input/output system (BIOS), which controls certain basic functions of processing system 20.

Further illustrated are an input/output (I/O) adapter 27 and a communications adapter 26 coupled to system bus 33. I/O adapter 27 may be a small computer system interface (SCSI) adapter that communicates with a hard disk 23 and/or a tape storage drive 25 or any other similar component. I/O adapter 27, hard disk 23, and tape storage device 25 are collectively referred to herein as mass storage 34. Operating system 40 for execution on processing system 20 may be stored in mass storage 34. A network adapter 26 interconnects system bus 33 with an outside network 36 enabling processing system 20 to communicate with other such systems.

A display (e.g., a display monitor) 35 is connected to system bus 33 by display adaptor 32, which may include a graphics adapter to improve the performance of graphics intensive applications and a video controller. In one aspect of the present disclosure, adapters 26, 27, and/or 32 may be connected to one or more I/O busses that are connected to system bus 33 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 33 via user interface adapter 28 and display adapter 32. A keyboard 29, mouse 30, and speaker 31 may be interconnected to system bus 33 via user interface adapter 28, which may include, for example, a Super I/O chip integrating multiple device adapters into a single integrated circuit.

In some aspects of the present disclosure, processing system 20 includes a graphics processing unit 37. Graphics processing unit 37 is a specialized electronic circuit designed to manipulate and alter memory to accelerate the creation of images in a frame buffer intended for output to a display. In general, graphics processing unit 37 is very efficient at manipulating computer graphics and image processing, and has a highly parallel structure that makes it more effective than general-purpose CPUs for algorithms where processing of large blocks of data is done in parallel.

Thus, as configured herein, processing system 20 includes processing capability in the form of processors 21, storage capability including system memory (e.g., RAM 24), and mass storage 34, input means such as keyboard 29 and mouse 30, and output capability including speaker 31 and display 35. In some aspects of the present disclosure, a portion of system memory (e.g., RAM 24) and mass storage 34 collectively store an operating system such as the AIX® operating system from IBM Corporation to coordinate the functions of the various components shown in processing system 20.

The present techniques may be implemented as a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some examples, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to aspects of the present disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various aspects of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Set forth below are some embodiments of the foregoing disclosure:

Embodiment 1: A method for determining robustness of a discrete fracture network (DFN) permeability estimate, the method comprising: receiving a DFN of an earth formation of interest, the DFN comprising a plurality of connected fractures; determining a directional equivalent permeability of the plurality of connected fractures of the DFN using a numerical upscaling method; and determining the robustness of the directional equivalent permeability.

Embodiment 2: The method of claim 1, wherein the directional equivalent permeability is a first directional equivalent permeability, and wherein determining the robustness of the first directional equivalent permeability comprises comparing the directional equivalent permeability to a second directional equivalent permeability.

Embodiment 3: The method of claim 2, wherein comparing further comprises comparing smoothness between the first directional equivalent permeability and the second directional equivalent permeability.

Embodiment 4: The method of claim 2, wherein comparing further comprises calculating a difference between the first directional equivalent permeability to the second directional equivalent permeability, where the first directional equivalent permeability is scaled by a constant factor.

Embodiment 5: The method of claim 4, wherein the difference represents a difference in a smoothness of a graphical representation of the first directional equivalent permeability and the second directional equivalent permeability.

Embodiment 6: The method of claim 1, wherein determining the robustness of the directional equivalent permeability comprises computing a robustness measure based on a change in the directional equivalent permeability.

Embodiment 7: The method of claim 6, wherein the change in the directional equivalent permeability includes at least one selected from the group consisting of: a number of steps between neighboring angles, a size of steps between neighboring angles, a slope of an equivalent permeability with changing direction, a variance measure computed with changes in an equivalent permeability with direction.

Embodiment 8: The method of claim 6, wherein the robustness measure of the directional equivalent permeability is compared with the robustness measures from another DFN.

Embodiment 9: The method of claim 1, further comprising: cropping the DFN prior to applying Oda's method.

Embodiment 10: The method of claim 1, further comprising: collecting a core sample of the earth formation of interest.

Embodiment 11: The method of claim 10, further comprising: generating the DFN of the earth formation of interest from the core sample.

Embodiment 12: The method of claim 1, further comprising: performing an action relating to the earth formation of interest using the first directional equivalent permeability.

Embodiment 13: The method of claim 12, wherein the action comprises: aligning a drill in a direction determined by the first directional equivalent permeability.

Embodiment 14: The method of claim 12, wherein the action comprises: performing in-fill drilling in a direction determined by the first directional equivalent permeability.

Embodiment 15: The method of claim 12, wherein the action comprises performing a reservoir stimulation in a direction determined by the first directional equivalent permeability.

Embodiment 16: The method of claim 1, wherein the numerical upscaling method comprises performing a perfect fit analysis.

Embodiment 17: A system for determining robustness of a discrete fracture network (DFN) permeability estimate, the system comprising: a memory having computer readable instructions; and a processing device for executing the computer readable instructions, the computer readable instructions comprising: receiving a DFN of an earth formation of interest, the DFN comprising a plurality of connected fractures; determining a first directional equivalent permeability of the plurality of connected fractures of the DFN using a numerical upscaling method; determining a second directional equivalent permeability of the plurality of connected fractures of the DFN using Oda's method; determining a robustness of the first directional equivalent permeability by comparing the first directional equivalent permeability to the second directional equivalent permeability; and performing an action relating to the earth formation of interest using the first directional equivalent permeability.

Embodiment 18: The system of claim 17, wherein the performing the action comprises: aligning a drill in a direction determined by the first directional equivalent permeability.

Embodiment 19: The system of claim 17, wherein comparing the first directional equivalent permeability to the second directional equivalent permeability comprises calculating a difference between the first directional equivalent permeability to the second directional equivalent permeability.

Embodiment 20: The system of claim 19, wherein the difference represents a difference in a smoothness of a graphical representation of the first directional equivalent permeability and the second directional equivalent permeability.

The descriptions of the various examples of the present disclosure have been presented for purposes of illustration, but are not intended to be exhaustive or limited to the embodiments disclosed. Many modifications and variations will be apparent to those of ordinary skill in the art without departing from the scope and spirit of the described techniques. The terminology used herein was chosen to best explain the principles of the present techniques, the practical application or technical improvement over technologies found in the marketplace, or to enable others of ordinary skill in the art to understand the techniques disclosed herein.

Additionally, the term "about" is intended to include the degree of error associated with measurement of the particular quantity based upon the equipment available at the time of filing the application. For example, "about" can include a range of ±8% or 5%, or 2% of a given value.

While one or more embodiments have been shown and described, modifications and substitutions may be made thereto without departing from the spirit and scope of the invention. Accordingly, it is to be understood that the present invention has been described by way of illustrations and not limitation.

What is claimed is:

1. A method for determining robustness of a discrete fracture network (DFN) permeability estimate, the method comprising:
   collecting a core sample of an earth formation of interest;
   generating the DFN of the earth formation of interest from the core sample;
   receiving a DFN of the earth formation of interest, the DFN comprising a plurality of connected fractures;
   determining, by a processing device, a directional equivalent permeability of the plurality of connected fractures of the DFN using a numerical upscaling method by capturing a series of slices taken incrementally about a center point of the DFN;
   determining, by the processing device, the robustness of the directional equivalent permeability; and
   performing an action relating to the earth formation of interest using the directional equivalent permeability, the action comprising aligning a tool in a direction determined by the directional equivalent permeability.

2. The method of claim 1, wherein the directional equivalent permeability is a first directional equivalent permeability, and wherein determining the robustness of the first directional equivalent permeability comprises comparing the directional equivalent permeability to a second directional equivalent permeability.

3. The method of claim 1, wherein determining the robustness of the directional equivalent permeability comprises computing a robustness measure based on a change in the directional equivalent permeability.

4. The method of claim 3, wherein the change in the directional equivalent permeability includes at least one selected from the group consisting of: a number of steps between neighboring angles, a size of steps between neighboring angles, a slope of an equivalent permeability with changing direction, a variance measure computed with changes in an equivalent permeability with direction.

5. The method of claim 3, wherein the robustness measure of the directional equivalent permeability is compared with the robustness measures from another DFN.

6. The method of claim 1, wherein the action comprises: performing in-fill drilling in a direction determined by the directional equivalent permeability.

7. The method of claim 1, wherein the action comprises: performing a reservoir stimulation in a direction determined by the directional equivalent permeability.

8. The method of claim 1, wherein the numerical upscaling method comprises performing a perfect fit analysis.

9. A method for determining robustness of a discrete fracture network (DFN) permeability estimate, the method comprising:
   receiving a DFN of an earth formation of interest, the DFN comprising a plurality of connected fractures;
   determining, by a processing device, a directional equivalent permeability of the plurality of connected fractures of the DFN using a numerical upscaling method;
   determining, by the processing device, the robustness of the directional equivalent permeability; and
   performing an action relating to the earth formation of interest using the directional equivalent permeability, the action comprising aligning a tool in a direction determined by the directional equivalent permeability,
   wherein the directional equivalent permeability is a first directional equivalent permeability, and wherein determining the robustness of the first directional equivalent permeability comprises comparing the directional equivalent permeability to a second directional equivalent permeability, and
   wherein comparing further comprises comparing smoothness between the first directional equivalent permeability and the second directional equivalent permeability.

10. The method of claim 9, wherein comparing further comprises calculating a difference between the first directional equivalent permeability to the second directional equivalent permeability, where the first directional equivalent permeability is scaled by a constant factor.

11. The method of claim 10, wherein the difference represents a difference in a smoothness of a graphical representation of the first directional equivalent permeability and the second directional equivalent permeability.

12. A system for determining robustness of a discrete fracture network (DFN) permeability estimate, the system comprising:
   a memory having computer readable instructions; and
   a processing device for executing the computer readable instructions, the computer readable instructions comprising:
      receiving a DFN of an earth formation of interest, the DFN comprising a plurality of connected fractures;
      determining a first directional equivalent permeability of the plurality of connected fractures of the DFN using a numerical upscaling method by capturing a first series of slices taken incrementally about a center point of the DFN;
      determining a second directional equivalent permeability of the plurality of connected fractures of the DFN using Oda's method by capturing a second series of slices taken incrementally about a center point of the DFN, wherein the DFN is cropped to fit the second series of slices;
      determining a robustness of the first directional equivalent permeability by comparing the first directional equivalent permeability to the second directional equivalent permeability; and
      performing an action relating to the earth formation of interest using the first directional equivalent permeability, wherein the performing the action comprises aligning a drill in a direction determined by the first directional equivalent permeability.

13. The system of claim 12, wherein comparing the first directional equivalent permeability to the second directional equivalent permeability comprises calculating a difference between the first directional equivalent permeability to the second directional equivalent permeability.

14. The system of claim 13, wherein the difference represents a difference in a smoothness of a graphical representation of the first directional equivalent permeability and the second directional equivalent permeability.

* * * * *